(12) United States Patent
Shoshani (10) Patent No.: US 9,820,911 B2
(45) Date of Patent: Nov. 21, 2017

(54) DEVICE FOR TREATMENT OF DEPRESSION, ANXIETY AND PAIN

(71) Applicant: Abraham Shoshani, Jerusalem (IL)

(72) Inventor: Abraham Shoshani, Jerusalem (IL)

(*) Notice: Subject to any disclaimer, the term of this patent is extended or adjusted under 35 U.S.C. 154(b) by 691 days.

(21) Appl. No.: 14/330,054

(22) Filed: Jul. 14, 2014

(65) Prior Publication Data

US 2015/0213724 A1  Jul. 30, 2015

(30) Foreign Application Priority Data

Jan. 29, 2014  (IL) .......................................... 230715

(51) Int. Cl.
| | |
|---|---|
| *G09B 5/00* | (2006.01) |
| *A61H 39/04* | (2006.01) |
| *A61N 1/04* | (2006.01) |
| *A61N 2/00* | (2006.01) |
| *A61H 39/00* | (2006.01) |
| *A61N 1/36* | (2006.01) |

(52) U.S. Cl.
CPC ........... *A61H 39/04* (2013.01); *A61H 39/002* (2013.01); *A61N 1/0408* (2013.01); *A61N 1/0476* (2013.01); *A61N 1/36014* (2013.01); *A61N 2/004* (2013.01); *A61N 2/008* (2013.01); *A61H 2201/0157* (2013.01); *A61H 2201/0207* (2013.01); *A61H 2201/0214* (2013.01); *A61H 2201/10* (2013.01); *A61H 2201/1695* (2013.01); *A61H 2205/125* (2013.01)

(58) Field of Classification Search
CPC ..................................... G09B 5/00; A61N 1/04
USPC .......................................................... 607/54
See application file for complete search history.

(56) References Cited

U.S. PATENT DOCUMENTS

| | | | | |
|---|---|---|---|---|
| 5,007,433 | A * | 4/1991 | Hermsdorffer | A61B 5/483 600/555 |
| 6,742,289 | B2 * | 6/2004 | Celmo | A43B 7/1465 36/141 |
| 8,075,501 | B2 * | 12/2011 | Miller | A43B 7/141 600/587 |
| 2004/0000076 | A1 * | 1/2004 | Celmo | A43B 7/1465 36/141 |

(Continued)

FOREIGN PATENT DOCUMENTS

| | | |
|---|---|---|
| CN | 2603671 | 10/2002 |
| GB | 2472168 | 1/2011 |

(Continued)

*Primary Examiner* — Sam Yao
*Assistant Examiner* — Alvin Carlos
(74) *Attorney, Agent, or Firm* — Edward Langer; ADV & Patent Attorney (57) ABSTRACT

A device (100) for the treatment of depression, anxiety and pain, the device comprising: a plurality of adjacent dots (11) or other shapes, each comprising means for providing a signal being sensible by a touch sense, the signal comprising mechanical signal and/or electrical signal and/or temperature signal and/or magnetic signal; and a controller (32) for executing each of the means independently, for providing pre-programmed shapes (30, 40, 40A, 40B, 42, 46, 48, 50, 52, 54) being sensible by the touch sense, thereby allowing treating the depression, anxiety and pain by generating to the brain, signals resembling the pre-programmed shapes (30, 40, 40A, 40B, 42, 46, 48, 50, 52, 54) through the signals being sensible by the touch sense.

22 Claims, 10 Drawing Sheets

(56) References Cited

U.S. PATENT DOCUMENTS

| | | | |
|---|---|---|---|
| 2005/0240253 A1* | 10/2005 | Tyler | A61B 5/0492 607/134 |
| 2006/0064139 A1* | 3/2006 | Chung | A61M 21/00 607/45 |
| 2006/0161218 A1* | 7/2006 | Danilov | A61B 5/0492 607/45 |
| 2007/0250119 A1* | 10/2007 | Tyler | A61N 1/36014 607/2 |
| 2009/0312817 A1* | 12/2009 | Hogle | A61B 5/0492 607/54 |
| 2011/0168685 A1* | 7/2011 | Naidu | H05B 3/10 219/201 |

FOREIGN PATENT DOCUMENTS

| | | |
|---|---|---|
| KR | 100917430 | 9/2009 |
| WO | WO2006081883 | 10/2006 |
| WO | WO2010033055 | 3/2010 |
| WO | WO2011089475 | 7/2011 |

* cited by examiner

DEVICE FOR TREATMENT OF DEPRESSION, ANXIETY AND PAIN

TECHNICAL FIELD

The present invention relates to the field of medical aid devices. More particularly, the invention relates to a device for treatment of depression, anxiety and pain.

BACKGROUND ART

According to the World Health Organization, 121 million people worldwide suffer from depression, only 25% of whom have access to effective treatment.

The majority of patients are treated with medication, although about 60% of these patients are not helped by the medication. Approximately 29% of Americans suffer from anxiety at some point in their lives.

A further approximately 15% of patients suffering depression are helped with magnetic field and electroconvulsive therapy. A small percentage of people suffer from Seasonal Affective Disorder (SAD), and can be helped with light therapy.

Currently accepted medical treatments for depression include medication, psychotherapy, transcranial magnetic stimulation (TMS—therapy using magnetic fields); electroconvulsive therapy (ECT), and light treatment for SAD.

There is also scientific evidence to back up the use of alternative methods such as meditation and yoga, but there is no conclusive scientific evidence that proves any benefit from reflexology or acupuncture on such illnesses.

ECT and TMS are very expensive treatments, costing tens of thousands of dollars as an ambulatory care treatment using a technician and a doctor. Use of a light therapy device costs the patient US$100-400; it only helps 1-10% of the patient population; and it is only useful for seasonally affected patients.

In a patent search carried out by the Applicant in Google Patents, and other patent databases, no patent publication has been found that intends to solve depression and anxiety problems.

It is an object of the present invention to provide a solution for the abovementioned problems, and other problems of the prior art.

The present invention will help people who have no access to an effective treatment, as well as patients who are not helped by currently existing medications and treatments.

Other objects and advantages of the invention will become apparent as the description proceeds.

SUMMARY OF THE INVENTION

A device (100) for the treatment of depression, anxiety and pain, the device comprising:
  a plurality of adjacent dots (11) or other shapes, each comprising means for providing a signal being sensible by a touch sense, the signal comprising mechanical signal and/or electrical signal and/or temperature signal and/or magnetic signal; and
  a controller (32) for executing each of the means independently, for providing pre-programmed shapes (30, 40, 40A, 40B, 42, 46, 48, 50, 52, 54) being sensible by the touch sense,
thereby allowing treating the depression, anxiety and pain by generating to the brain, signals resembling the pre-programmed shapes (30, 40, 40A, 40B, 42, 46, 48, 50, 52, 54) through the signals being sensible by the touch sense.

The pre-programmed shapes (30, 40, 40A, 40B, 42, 46, 48, 50, 52, 54) being sensible by the touch sense may comprise a procedure of increasing resolution of lines (40, 40A, 40B, 42) or of other shapes,
thereby utilizing the touch sense for brain discrimination exercises, rather than brain discrimination exercises applied by meditation treatment.

The procedure of increasing resolution of lines (40, 40A, 40B, 42) or of other shapes may comprise maintaining a constant number of lines.

The procedure of increasing resolution of lines (40, 40A, 40B, 42) or of other shapes may comprise providing a single distance at each step.

The procedure of increasing resolution of lines (40, 40A, 40B, 42) or of other shapes may comprise providing a plurality of distances at each step.

The pre-programmed shapes (30, 40, 40A, 40B, 42, 46, 48, 50, 52, 54) being sensible by the touch sense may comprise a procedure of providing shapes (46) comprising empty segments (48) thereof,
thereby utilizing the touch sense for brain completion exercises.

The pre-programmed shapes (30, 40, 40A, 40B, 42, 46, 48, 50, 52, 54) being sensible by the touch sense may comprise a procedure of
  providing a line or shape (50),
  then of providing a portion (52) of the line or shape (50), and
  then of providing the said line or shape (54),
thereby utilizing the touch sense for producing an expectation, produced by the line or shape (50) and by the portion (52), and for producing a fulfillment of the expectation, produced by said line or shape (54) again.

The plurality of adjacent dots (11) or other shapes may comprise one or more groups (10) of shiftable and retractable pins (11), each of the pins (11) being substantially perpendicular to a surface on which the pins are disposed; and
  the controller (32) is adapted for controlling the operation of shifting and retracting each of the pins (11) individually; and
  the device (100) may further comprise a computerized mechanism (34) for instructing the controller (32) to shift/retreat each of the pins individually, according to a script, being a group of timed instructions;
  thereby generating mechanical stimulation signal/pulse to a human organ, according to a script.

The device may further comprise a mechanism for heating the plurality of adjacent dots (11) or other shapes, for allowing the device to produce a heating pulse/signal.

The device may further comprise a mechanism for chilling the plurality of adjacent dots (11) or other shapes, for allowing the device to produce a chilling pulse/signal.

The device may further comprise a mechanism for electrifying the plurality of adjacent dots (11) or other shapes, for allowing the device to produce an electric pulse/signal.

The device may further comprise an electromagnetic mechanism, for magneticizing the plurality of adjacent dots (11) or other shapes, thereby allowing the device to produce a magnetic pulse/signal.

Each command of the script may define a form of the pulse/signal.

The form may be an intensity and/or duration and/or rhythm and/or a cycle.

Each of the dots (11) or other shapes may be heated individually.

All of the pins may be heated together by a heated liquid disposed around the pins when being in their retreated state.

Each of the pins may be chilled individually.

All of the pins may be chilled together by a chilling liquid disposed around the pins when being in their retreated state.

The surface may correspond to a surface of a human organ.

The human organ may constitute a palm and/or a foot and/or a sole, and/or a back, and/or a face.

The more sensitive a region of the human organ, the higher the density of the members of the group (10) of shiftable and retractable pins (11).

The pins may be shifted out in a geometric form.

The pins may be shifted in a partial geometric form, thereby allowing a patient's brain to complete the full form.

The members of the group (10) of shiftable and retractable pins (11) may be arranged in a matrix form.

The device may further comprise:
- a first perforated plate (12) wherein the pins (11) are shiftable through the perforation;
- a second plate (14);
- a closed space (38) between the plates, filled with a liquid (42); and
- a heating/chilling body (40) disposed in the liquid (42), for heating/chilling the liquid (42),
thereby heating/cooling all of the pins when dipped in the liquid.

The plurality of adjacent dots (11) or other shapes may comprise an electrical mask comprising a plurality of electrical outputting dots or of other shapes.

The reference numbers have been used to point out elements in the embodiments described and illustrated herein, in order to facilitate the understanding of the invention. They are meant to be merely illustrative, and not limiting. Also, the foregoing embodiments of the invention have been described and illustrated in conjunction with systems and methods thereof, which are meant to be merely illustrative, and not limiting.

BRIEF DESCRIPTION OF DRAWINGS

Preferred embodiments, features, aspects and advantages of the present invention are described herein in conjunction with the following drawings:

FIG. 4 is a sectional view that illustrates the cross-section A-A defined in FIG. 1. In FIG. 4 the pins are lifted up.

It should be understood that the drawings are not necessarily drawn to scale.

DESCRIPTION OF EMBODIMENTS

The present invention will be understood from the following detailed description of preferred embodiments ("best mode"), which are meant to be descriptive and not limiting. For the sake of brevity, some well-known features, methods, systems, procedures, components, circuits, and so on, are not described in detail.

The present invention is directed to a device for treating depression, anxiety and pain.

The term "synapse" refers herein to a structure that permits a neuron (or nerve cell) to pass an electrical or chemical signal to another neuron The term "somato-sensory" refers herein to touch sense.

One of possible explanations for the development of depression is disturbance in the plasticity of the brain. The present invention is directed to improve the plasticity in synaptic activity of the brain, by transmitting touchable signals to the synapses.

Research studies in the field of neurobiology and clinical experiments have shown that by increasing somatosensory discrimination activity, it is possible to improve the condition of patients suffering from clinical depression and anxiety. This is supported also by initial clinical observations.

Through stimulation with special modulated signals to human organs such as foot sole, palm, and so on, the present invention gradually reduces the patient's nervous system's discrimination threshold.

By reducing the "noise" of sensoric and by using sensomotoric signals, a device thereof will improve the condition of patients suffering clinical depression and anxiety.

The technical innovation is introduced by activating a variable modality of generating pulses to sensitive parts of the patient's body. Such a device includes algorithms in the form of software files that will be stored to an electronic card as a result of tests conducted on the patient.

The terms "pulse" and "signal" refer herein to a time period of stimulation. For example, "an electric pulse" is an electric impact that takes a duration such as hundredths of a second, tenth of a second, etc, while "an electric signal" takes at least seconds.

The object is obtained by a device that generates stimulation signals/pulses on sensitive region(s) of the body of a patient, such as palms, hands, feet, soles, face, etc.

The stimulation signal can be controlled by a control system, which may be operated by computer software.

The stimulation signal can be in a form of mechanical force, electrical current, temperature (heat/cold), magnetic, and so on.

The stimulation signal may be sequential, intermittent, repeatable, non-repeatable, in a single pattern or a plurality of patterns, and so on.

According to one embodiment of the invention, the device is adapted to perform a plurality of stimulation signals simultaneously, such as electric pulse along with a heat pulse.

According to one embodiment of the invention, the stimulation device is adapted to incorporate a plurality of stimulation forms into the same device to stimulate the aforesaid sensitive areas of a patient's body.

The device may be designed as a mobile device, as well as a fixed device.

The device can be used by doctors, as well as a self-treatment device.

As a result of treatments with the stimulation device, an improvement may be seen in the condition of a patient suffering from depression, anxiety or pain.

According to one embodiment of the invention, the device uses a group of pins movable by a control system (which may be a computerized mechanism), wherein the end thereof is used as a stimulation terminal, such as means for producing a physical hit, a contact for generating electric pulse, a heating body for generating heat, and so on.

The group of movable pins may be ordered in a form of a matrix, i.e., a group of elements uniformly arranged in rows and columns, or in a different form, not necessarily with uniform dispersal. For example, in sensitive areas of a human body, the dispersal may be more condensed than in less sensitive areas of the human body.

According to one embodiment of the invention, the patient lies on a bed, with his lap flex by a bar that lifts them up. In this situation his feet are approached to the device (or the device is approached to the patient's foot soles. In the first stage, the device resets the pins by approaching each of the pins to the surface of the patient's foot sole. In this situation the stimulation takes place.

The stimulation may be in a form of a physical contact, electric current, magnetic field, heat/cold signal, through the pins, in different geometrical forms, intensities, resolutions, rhythms, repeatable, and so on, according to commands of a computerized command that runs algorithms thereof.

Figure 1:
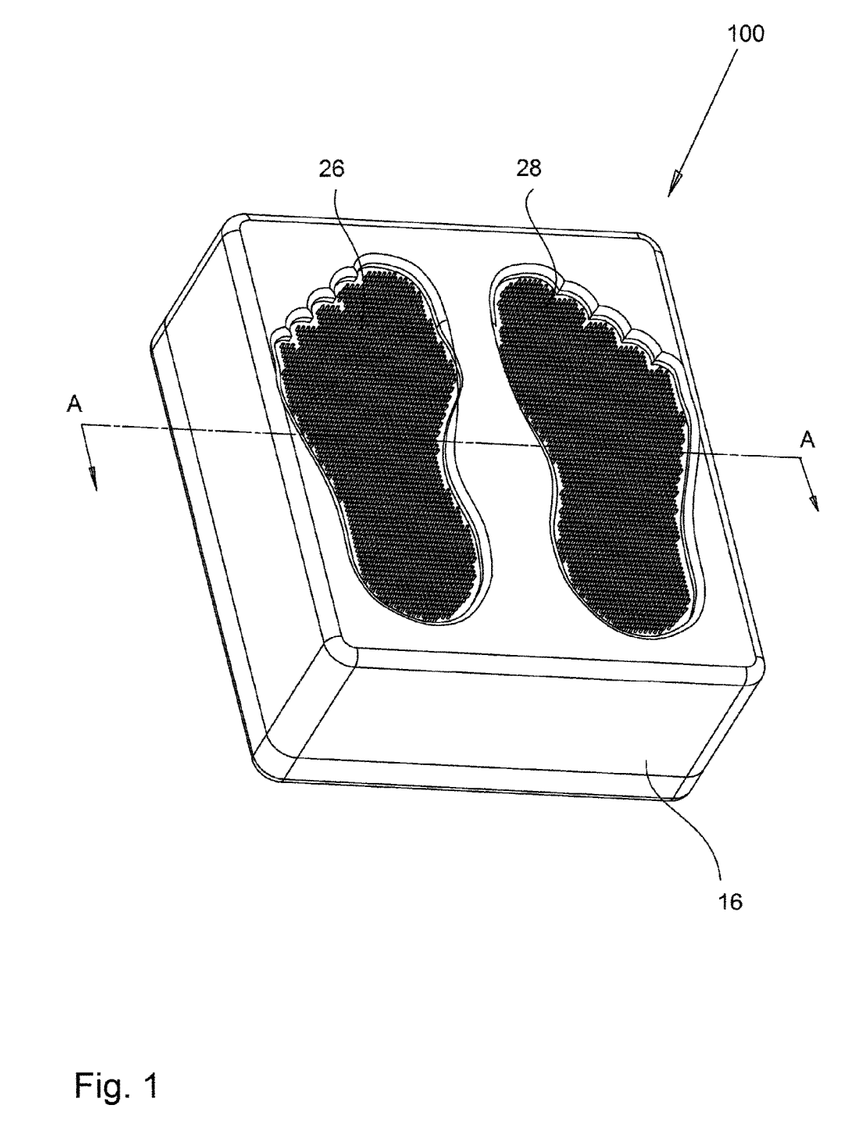
FIG. 1 pictorially illustrates a device for treatment of depression and anxiety, according to one embodiment of the invention.

FIG. 1 pictorially illustrates a device for treatment of depression and anxiety, according to one embodiment of the invention.

The device, which is marked herein by reference numeral 100, is adapted to stimulate the foot soles of a patient.

The device comprises a casing 16, wherein at the top side thereof are disposed two panels 26 and 28, correspondingly to human feet soles. In each panel is installed a matrix of movable pins, their movement being controlled by a control, as will be further detailed. The pins of the panels are depressed in order to allow placing thereon a human foot sole.

Figure 4:
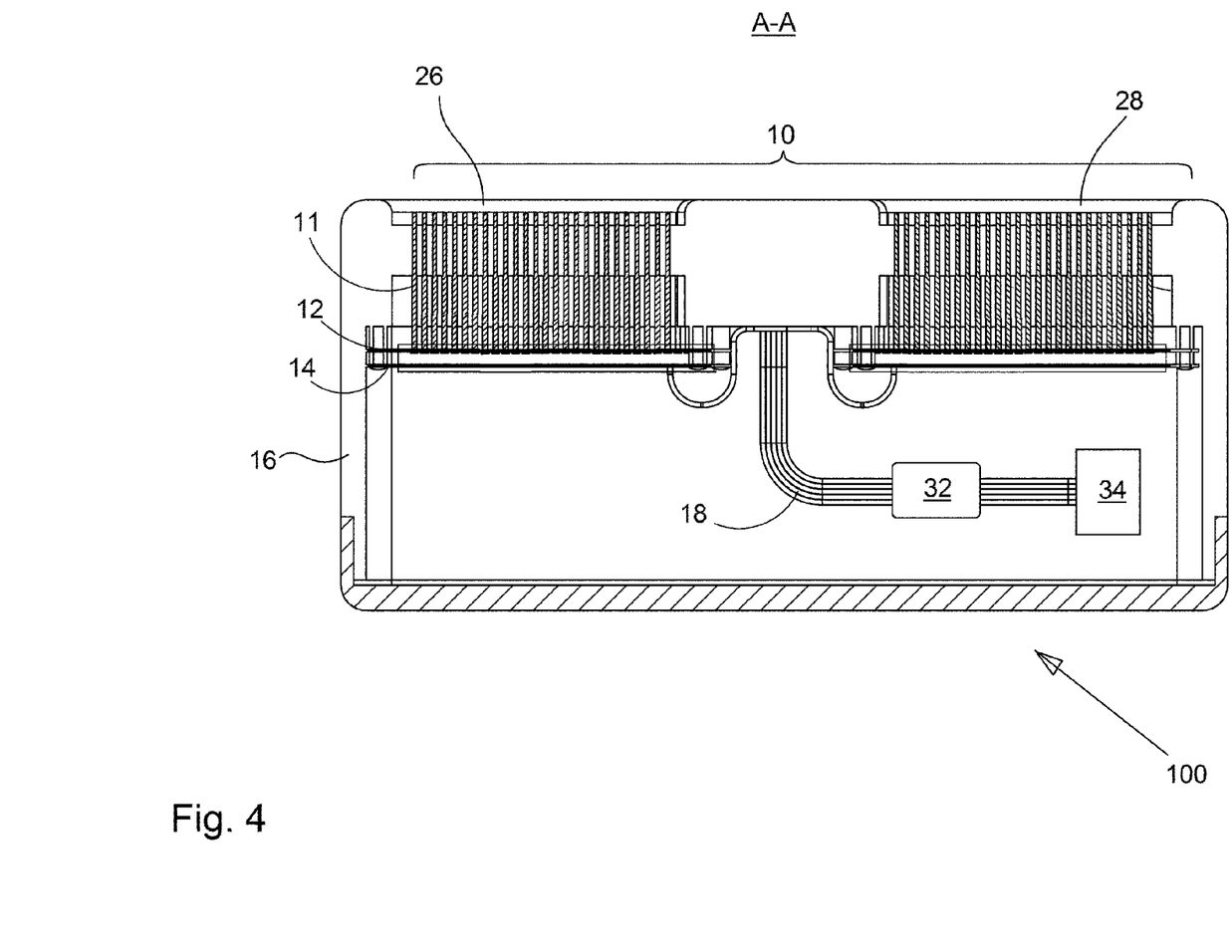

FIG. 1 also defines a cross-section A-A, the result of which is illustrated in FIG. 4.

Figure 2:
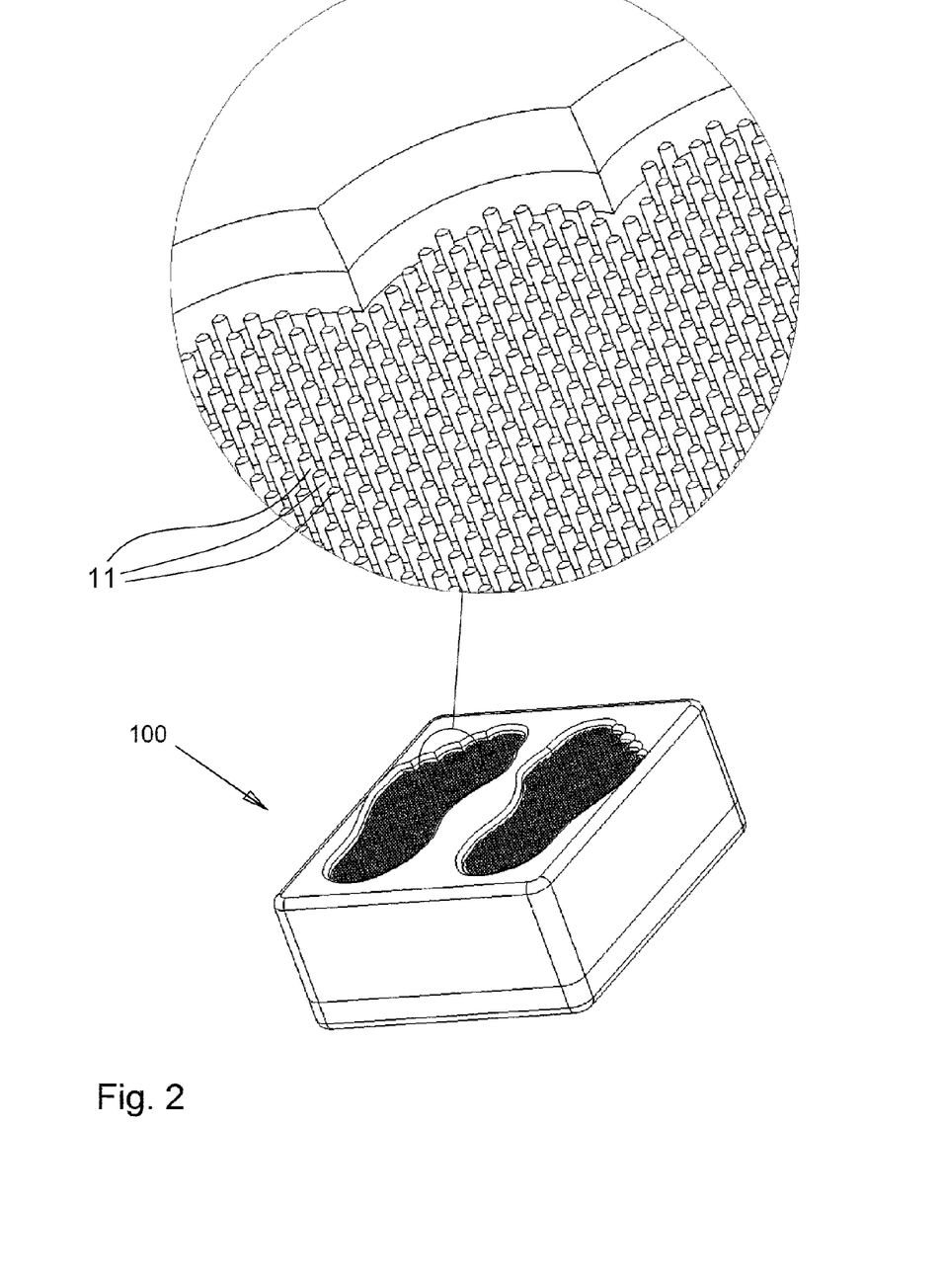
FIG. 2 further details the pin matrix of FIG. 1, by focusing the "magnifying glass" on pins of a matrix.

FIG. 2 further details the pin matrix of FIG. 1, by focusing the "magnifying glass" on pins of a matrix.

In this example pins 11 are dispersed uniformly, but it should be noted that the pins arrangement may not be uniform as a result of treatment and/or technical considerations.

According to the embodiment of FIG. 2, the shape of each pin 11 is of a dot.

Figure 2A:
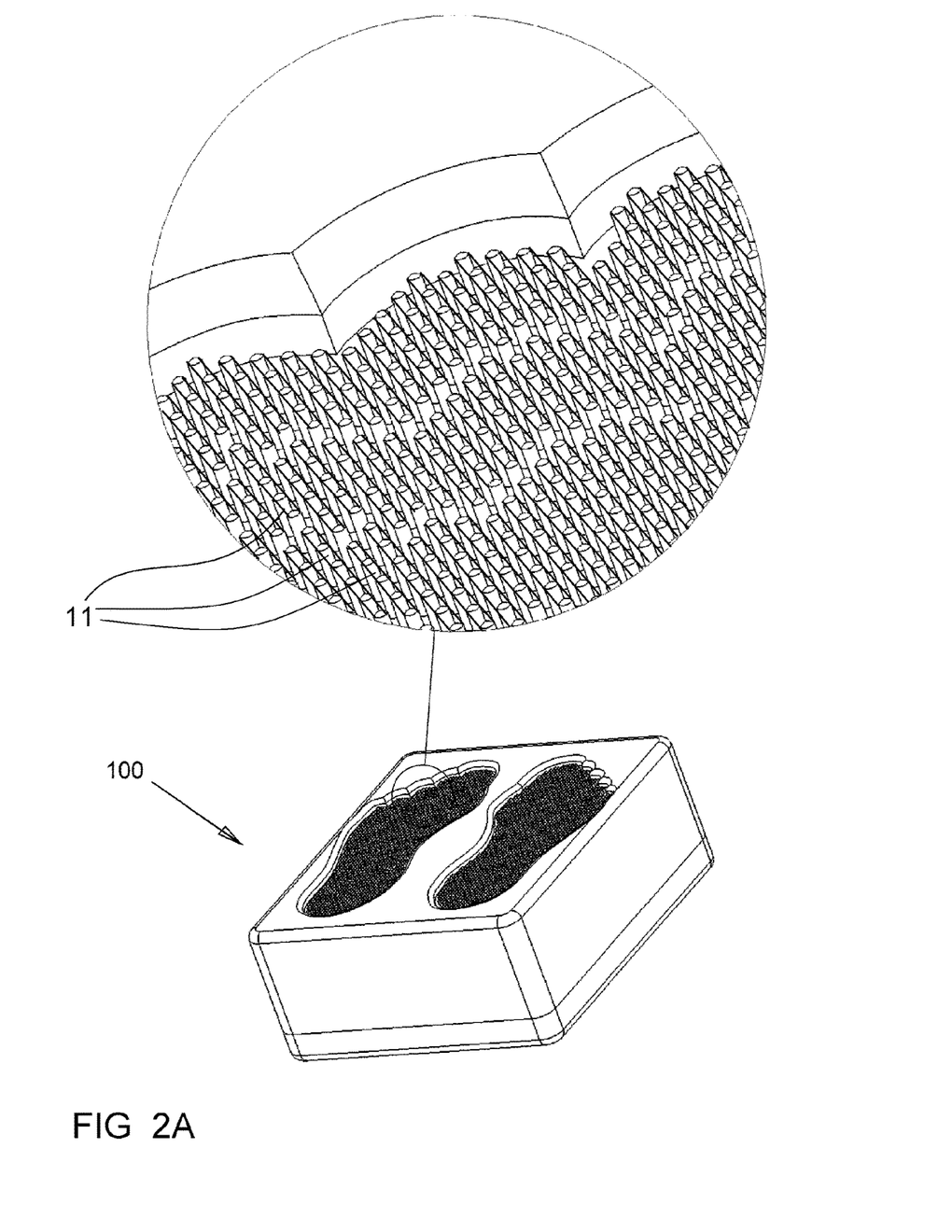
FIG. 2A. is similar to FIG. 2, except that the shape of each pin is of a line.

FIG. 2A is similar to FIG. 2, except that the shape of each pin is of a line.

According to another embodiment, the shape of each pin 11 may be a line or another shape.

In FIGS. 2 and 2A, all the illustrated pins 11 are elevated, but as will be described hereinafter, each of the pins 11 is movable and its state is changeable by a control system.

Figure 3:
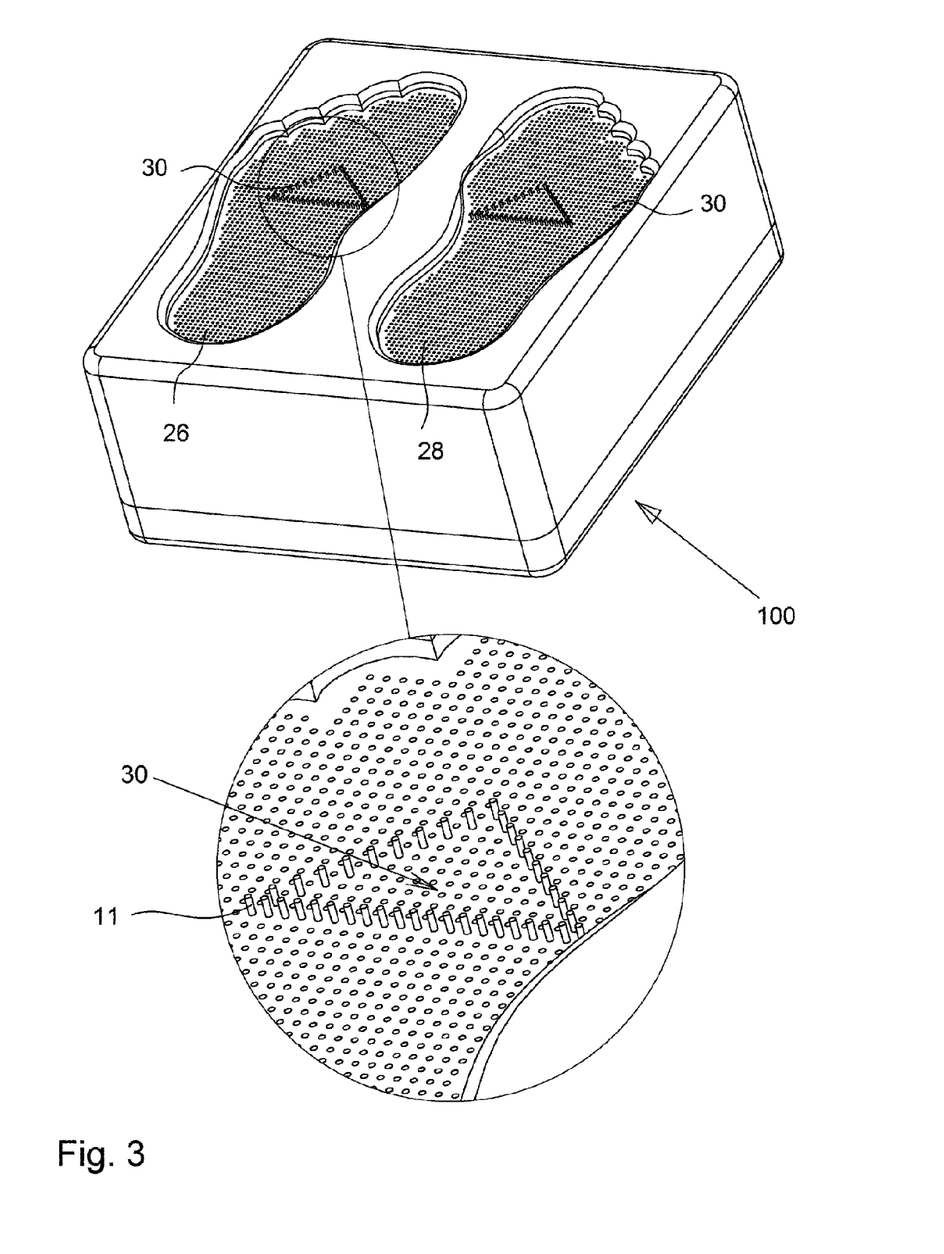
FIG. 3 further details the pins matrix of FIG. 2.

FIG. 3 further details the pins matrix of FIG. 2.

The plurality of pins 11 may provide a plurality of pre-selected shapes. In the example of FIG. 3, the plurality of pins 11 form a triangle 30, which is generated by elevating the corresponding pins 11, by a controlling mechanism thereof (not illustrated in this figure). Thus, each of pins 11 can be elevated and lowered by a control mechanism, according to commands from a computerized mechanism that runs algorithms thereof.

Triangle 30 may be generated by other means, rather than by mechanical means applied by pins 11, such as by electrical means, for supplying electrical current to the skin, or temperature means for heating or cooling dots or other shapes on the skin. The electrical means may apply an electrical mask including a plurality of electrical outputting dots or of other shapes. The temperature means may apply a plurality of heat or cool outputting dots or other shapes.

In general, the patient must sense by somato-sensory thereof, pre-determined shapes produced as a function of time.

A pre-selected procedure is executed, for applying the treatment. One procedure is somato-sensory discrimination, for transmitting to the brain of the patient, through touchable signals, such as of physical, electrical, or temperature signals, discrimination of lines or dots or other shapes in various resolutions.

Figure 3A:
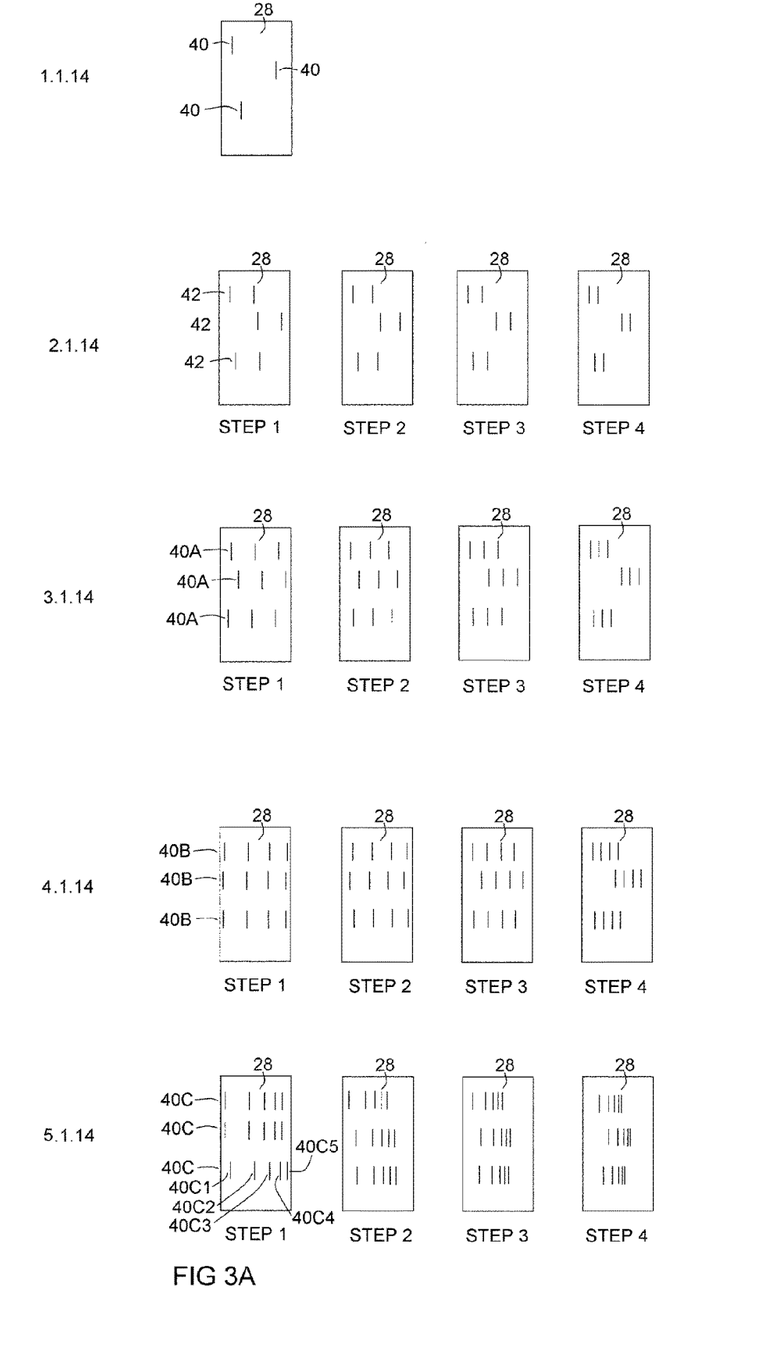
FIG. 3A depicts steps of a first procedure for applying the treatment.

FIG. 3A depicts steps of a first procedure for applying the treatment.

The discrimination of lines or other shapes may be applied by increasing the resolution of the lines or of the shapes from step to step. According to one embodiment, the number of lines is constant along the steps, for example 1 or 2 or 3 or 4, and the resolution being constant at every step, increases from one step to the next step, as exemplified below For example, at the first day (1.1.14) of treatment pins 11 within panel 28 may produce one line 40 or another shape, disposed at various locations of panel 28. Line 40 is not permanently produced, but rather is produced and cancelled repeatedly, e.g., produced for 20 seconds, cancelled for 10 seconds, the produced for 20 seconds or for 18 seconds, etc.

At the second day (2.1.14) of the treatment, pins 11 within panel 28 may produce two lines 42 or another shape, disposed at various locations of panel 28, wherein at the first step, the distance between lines 42 is 2.5 centimeters one from the other; at the second step, the distance between lines 42 is 2 centimeters one from the other; at the third step, the distance between lines 42 is 1.5 centimeters one from the other; and at the fourth step, the distance between lines 42 is 1 centimeters one from the other. Preferably, lines 42 are not permanently produced, but rather are produced and cancelled repeatedly.

At the third day (3.1.14) of the treatment, pins 11 within panel 28 may produce three lines 40A or another shape, disposed at various locations of panel 28, wherein at the first step, the distance between lines 40A is 2.5 centimeters one from the other; at the second step, the distance between lines 40A is 2 centimeters one from the other; at the third step, the distance between lines 40A is 1.5 centimeters one from the other; and at the fourth step, the distance between lines 40A is 1 centimeters one from the other. Preferably, lines 40A are not permanently produced, but rather are produced and cancelled repeatedly.

At the fourth day (4.1.14) of the treatment, pins 11 within panel 28 may produce four lines 40B or another shape, disposed at various locations of panel 28, wherein at the first step, the distance between lines 40B is 2.5 centimeters one from the other; at the second step, the distance between lines 40B is 2 centimeters one from the other; at the third step, the distance between lines 40B is 1.5 centimeters one from the other; and at the fourth step, the distance between lines 40B is 1 centimeters one from the other. Preferably, lines 40B are not permanently produced, but rather are produced and cancelled repeatedly.

According to one embodiment, the distance between the lines may be different within the same set of lines.

For example, at the fifth day (5.1.14) of the treatment, pins 11 within panel 28 may produce a set of five lines 40C including from left to right the lines 40C1, 40C2, 40C4, 40C4 and 4005, or another shape, disposed at various locations of panel 28, wherein at the first step, the distance between line 40C1 and 40C2 is 2.5 centimeters; the distance between line 40C2 and 40C3 is 2 centimeters; the distance between line 40C3 and 40C4 is 1.5 centimeters; and the distance between line 40C4 and 4005 is 1 centimeters.

At the second step, the distance between line 40C1 and 40C2 is 2 centimeters; the distance between line 40C2 and 40C3 is 1.6 centimeters; the distance between line 40C3 and 40C4 is 1.2 centimeters; and the distance between line 40C4 and 4005 is 0.8 centimeters;

And at the following steps, the distances decrease in relation to the previous step accordingly.

This signaling to the brain through the touchable signals, is applied for exercising brain discrimination in an improved manner, since it applies physical means, rather than brain discrimination exercises applied by pure cognitive affecting means applied by known meditation treatments.

Figure 3B:
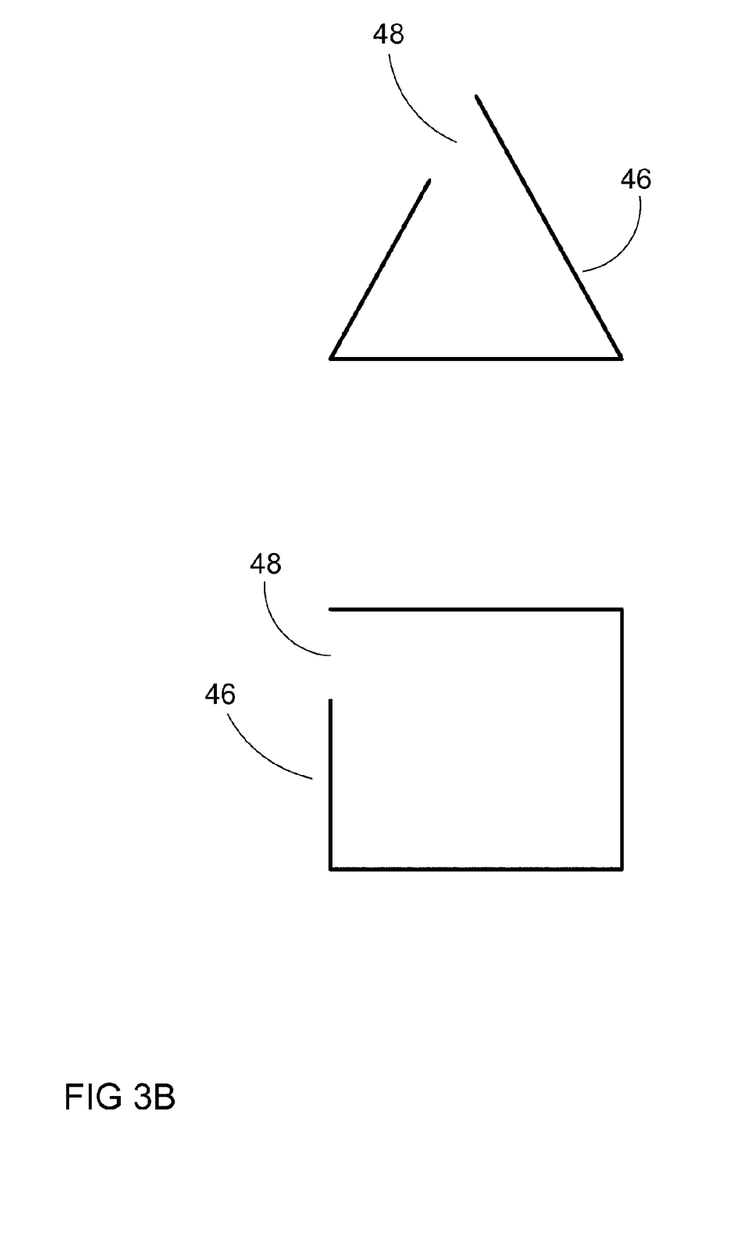
FIG. 3B depicts a second procedure for applying the treatment.

FIG. 3B depicts a second procedure for applying the treatment.

According to another procedure of treatment, for being applied by device 100, device 100 produces shapes, for being completed by the brain. For example, the shape for being completed by the brain may constitute a triangle 46 or a rectangle 46, each having an empty segment 48. Empty segment 48 is produced for being completed by the brain.

Figure 3C:
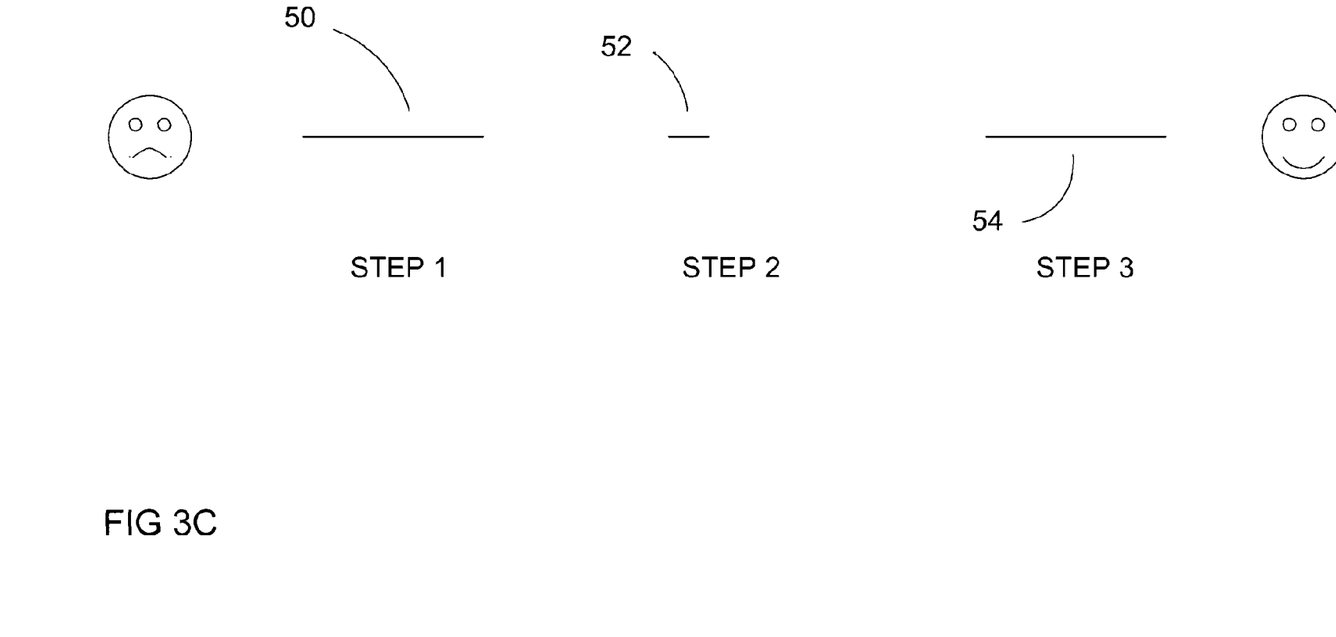
FIG. 3C depicts a third procedure for applying the treatment.

FIG. 3C depicts a third procedure for applying the treatment.

According to another procedure of treatment, for being applied by device 100, device 100 produces expectations for being fulfilled. The embodiment includes producing sequenced shapes, for producing expectations, and for being later completed by device 100.

For example, at the first step, device 100 produces a line 50; at the second step, device 100 produces one or more dots or other segments 52 being a portion of line 50. The patient expects the remainder of line 50. Then device 100 fulfils, at the third step, the expectation by producing a line 54 being similar to line 50.

Preferably, the shapes produced by device 100 are not permanently produced, but rather are produced and cancelled repeatedly.

A physical hit can be generated by elevating a pin, and then immediately retreating to its lowered state.

The pins may provide a plurality of stimulation forms. For example, the pin which is designed to generate a physical hit may also comprise a heating body which heats the pin. As a result, the pin not only hits the sole, but also provides a heat pulse.

A pin may also generate an electrical current. Thus, each pin may be used for generating a pulse of: physical, electrical, and temperature nature, in combination or not.

FIG. 4 is a sectional view that illustrates the cross-section A-A defined in FIG. 1. In FIG. 4 the pins are lifted up.

Figure 5:
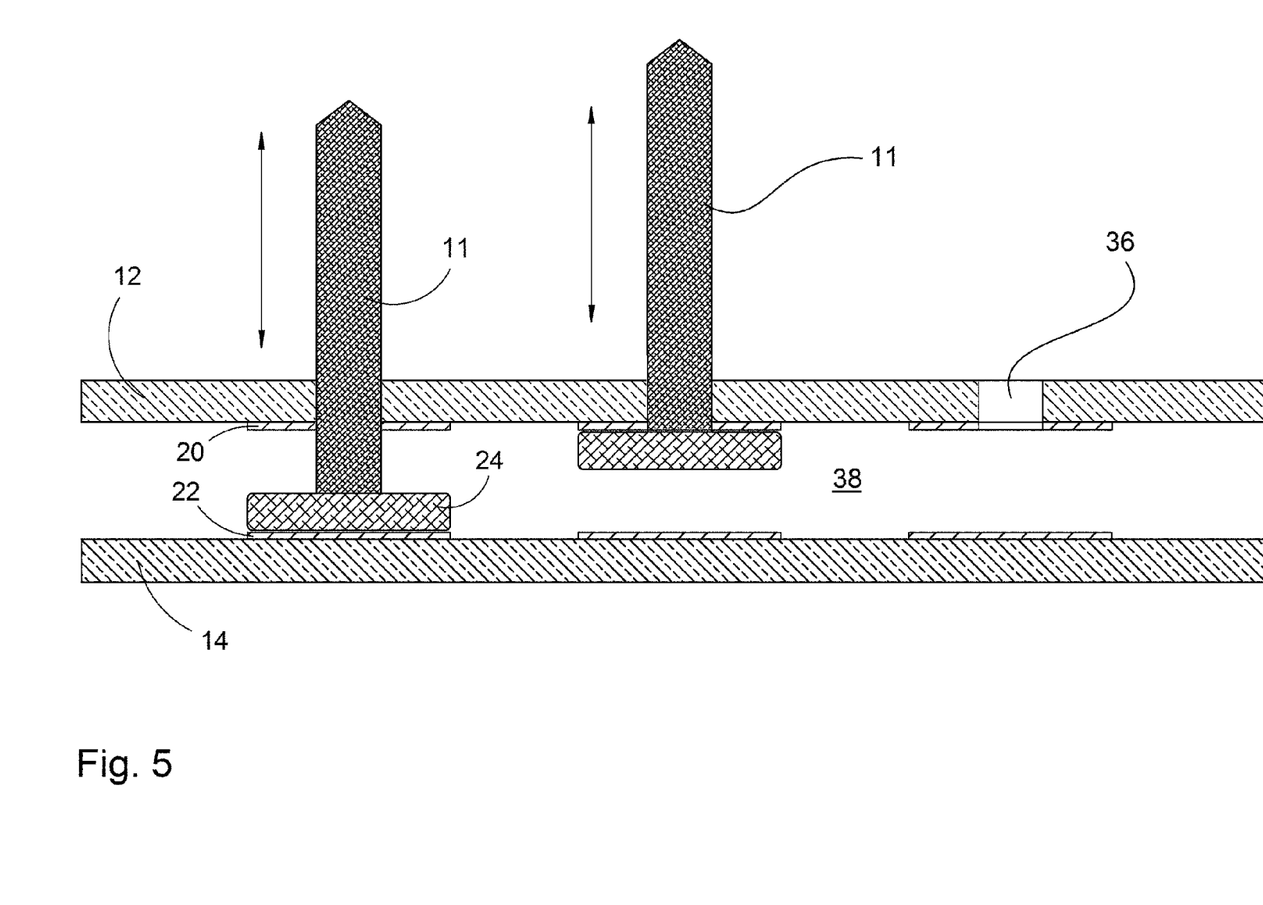
FIG. 5 is a sectional view that focuses on the electromechanical mechanism of shifting the pins.

FIG. 5 is a sectional view that focuses on the electromechanical mechanism of shifting the pins.

FIG. 5 illustrates two pins, the left one being lowered down, and the right one lifted up. Reference numeral 36 denotes a hole of the perforation of plate 12, from which the pin thereof has been "removed".

As mentioned, reference numeral 12 denotes a perforated plate. Each of the holes 36 of the perforated plate is a conduit used for passing therethrough a pin 11. It should be noted that each of the pins is perpendicularly shiftable to the surface of the panel at the pin's location.

Reference numeral 14 denotes a lower plate (in the figure's orientation). Reference numeral 20 denotes an upper electromagnet and reference numeral 22 denotes a lower electromagnet (in the figure's orientation). Reference numeral 24 denotes a ferric element, attached to pin 11.

It should be noted that one of the electromagnets 20 or 22 may be replaced by a spring, thereby obtaining a simplified mechanism. When using a spring instead of an electromagnet, each pin has two states: an idle state, wherein the spring pushes the pin towards on of the plates 12, 14; and an active state, where the pin is pulled to the opposite direction.

When the upper electromagnet 20 is activated, it pulls up the ferric element 24, and therefore the pin is lifted up. When the lower electromagnet 22 is activated, it pulls down the ferric element 24, and therefore the pin is lowered down.

As illustrated, the ferric element 24 is larger than the width of hole 36, and therefore the perforated plate 12 limits the movement of pin 11 upwards. In addition, plate 14 limits the movement of the pin downwards.

It should be noted that in FIG. 5, each of the pins has a tip in a conic form. This structure provides a tingle, which is a form of stimulation. Of course, the pin's tip may be dull.

Referring again to FIG. 4, each of the electromagnets is controlled by a controller 32. Thus, the controller is in charge of providing power to the upper electromagnet 20 and the lower electromagnet 22 of each of the pins.

The computerized mechanism 34 is in charge of instructing controller 32 to which electromagnet of the pins to provide power. The commands from the computerized mechanism to controller 32, and therefrom to the pins of matrix 10 are transferred via a bus 18.

The term "script" refers herein as to a group of timed instructions (to perform a physical operation by a machine).

The computerized mechanism may use scripts for activating the pins, and the stimulation thereof (heating, chilling, electrifying, etc.). For example, the triangle form 30 of the pins which is illustrated in FIG. 3 can "move" forth and back in a repeatable manner, while each of the pins is heated. Thus, the computerized mechanism "decides" when to lift up a pin, and when to lower a pin, and the controller is the mechanism that provides the power to the required electromagnets to perform the computerized mechanism's commands While the term "controller" refers herein to a mechanism for carrying out a physical operations, the term "computerized mechanism" refers herein a group of instructions to the controller. A computerized mechanism may include a CPU and memory for executing a program (which is a group of commands stored in the memory). Of course, presently a computerized mechanism can be implemented merely by a circuitry.

Preferably, the computerized mechanism may comprise a user interface, by which a user (doctor, therapist, the patient, etc.) selects the stimulation treatment (script), sets parameters of the treatment (such as the duration, the intensity of the pulses, etc). Using the user interface, the user also may determine the script, may define new stimulation scripts, and so on.

Preferably, the surface form of each of plates 12 that forms each of the panels 26 and 28 should correspond to a human foot sole, and in general to a human organ to be stimulated. However, in order to facilitate the understanding of the invention, in the accompanying figures the plate 12 is flat.

A magnetic pulse/signal can be generated by an electromagnetic mechanism. An electric pulse/signal can be generated by a circuitry for this purpose, which presently is well known.

As per a magnetic pulse/signal, the device can be designed such that when a pin is lifted up, it closes a circuit which generates an electric/magnetic pulse/signal. Thus, the same mechanism that moves the pins may also be used for generating a physical hit, a heat/chill pulse/signal, and so on.

Figure 6:
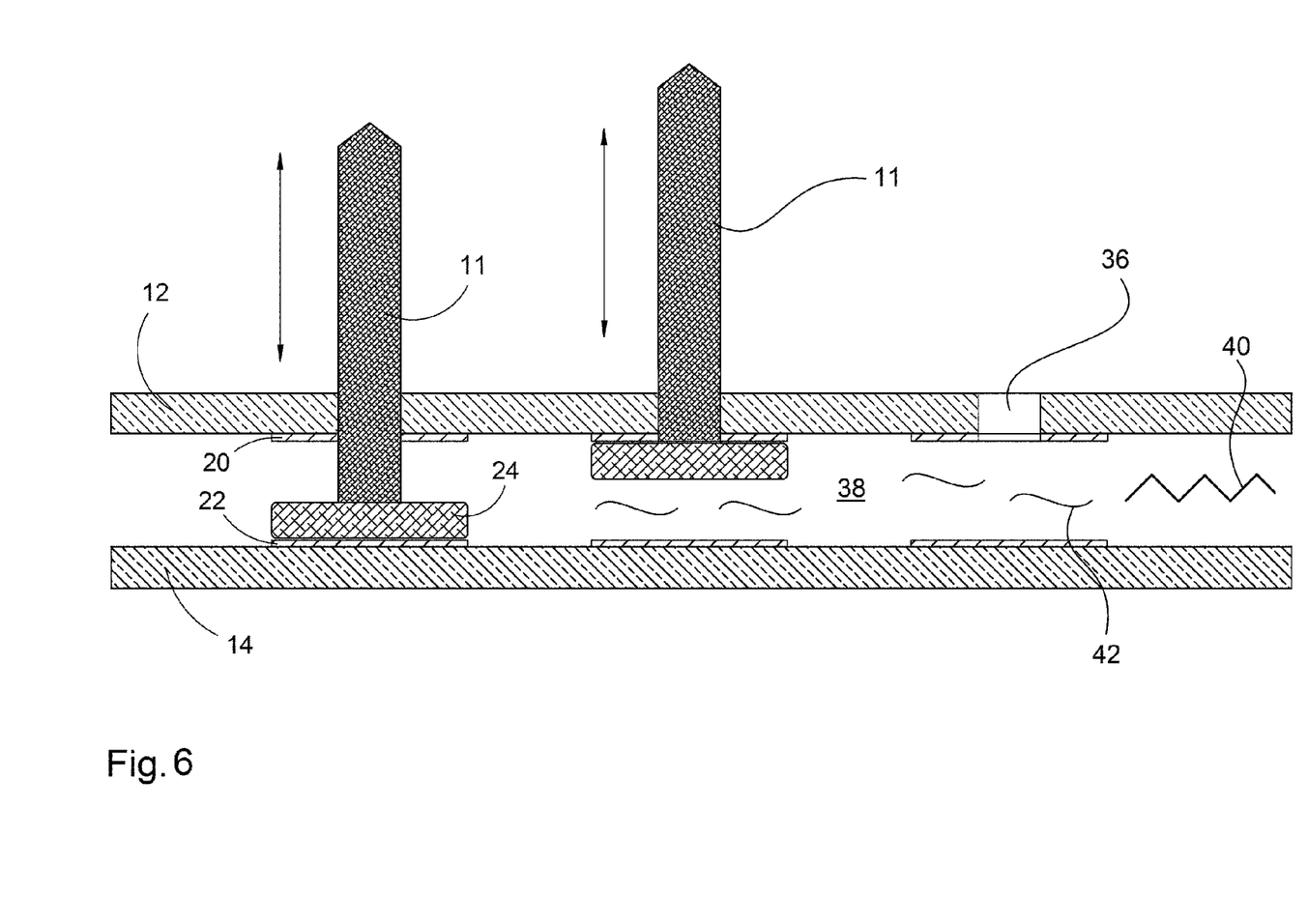
FIG. 6 is a sectional view that focuses on the heating mechanism of the pins.

FIG. 6 is a sectional view that focuses on the heating mechanism of the pins.

According to this embodiment of the invention, the space 38 between the upper and lower plate can be filled with liquid 42, which can be heated by a heating body 40. As a result, when the pins are in their lower state, i.e., dipped in the heated liquid 42, they are heated, and when they are lifted up, the heat is propagated to the human body at the contact points. This mechanism is simpler than heating each of the pins by its individual heating body. The same mechanism can be applied to chilling the pins.

In the figures and/or description herein, the following reference numerals (Reference Signs List) have been mentioned:

numeral 100 denotes a device for treatment of depression and anxiety, according to one embodiment of the invention;
numeral 10 denotes a group of pins 11;
numeral 11 denotes a movable pin, controllable by a controller 32 by a computerized mechanism 34;
numeral 12 denotes a perforated plate;
numeral 14 denotes a lower plate, which limits the movement of each of the pins downwards (in the figures' orientation);
numeral 16 denotes a casing, wherein at the top side thereof are disposed two panels 26 and 28, correspondingly to human feet soles;
numeral 18 denotes a bus (a data communication channel) that passes commands from the computerized mechanism 34, to the controller 32;
numeral 20 denotes an upper electromagnet (in the figures' orientation);
numeral 22 denotes a lower electromagnet (in the figures' orientation);
numeral 24 denotes a ferric element;
numeral 26 denotes a left panel, correspondingly to a human left foot sole;
numeral 28 denotes a right panel, correspondingly to a human right foot sole;
numeral 30 denotes a triangle form, generated from the pins 11 of matrix 10;
numeral 32 denotes a controller;
numeral 34 denotes a computerized mechanism (e.g., that includes a CPU and memory);
numeral 36 denotes a hole in a perforation in plate 12;
numeral 38 denotes a space between plate 12 and plate 14;
numerals 40, 40A, 40B, 40C, and 42 denote lines or set of lines produced;
numerals 40C1, 40C2, 40C3, 40C4 and 4005 denote single lines within a set of lines produced;
numeral 46 denotes a shape, such as a triangle or a rectangle or a circle, having an empty segment;
numeral 48 denotes an empty segment of the produced line or shape;
numeral 50 denotes a line or shape to be produced;
numeral 52 denotes a dot or another segment of the line or the other produced shape; and
numeral 54 denotes difference between two produced shapes.

The foregoing description and illustrations of the embodiments of the invention has been presented for the purposes of illustration. It is not intended to be exhaustive or to limit the invention to the above description in any form.

Any term that has been defined above and used in the claims, should to be interpreted according to this definition.

The reference numbers in the claims are not a part of the claims, but rather used for facilitating the reading thereof. These reference numbers should not be interpreted as limiting the claims in any form.

What is claimed is:

1. A device for treatment of depression, anxiety and pain, the device comprising:
   a plurality of adjacent dots each being a physical stimulus object, wherein said plurality of adjacent dots is adapted to be placed externally to a human body and comprises at least one group of shiftable and retractable pins arranged in a matrix form, each of said pins being perpendicular to a surface on which said pins are disposed,
   each of said plurality of adjacent dots comprising means for providing a physical stimulation pulse/signal being sensible by a touch sense, said pulse/signal being selected from a group consisting of: a mechanical signal, an electrical signal, a temperature signal, a magnetic signal; and
   a controller for executing each of said means independently, for providing pre-programmed spatial shapes produced and cancelled repeatedly, for being sensed by the touch sense,
   wherein said controller is adapted for controlling the operation of shifting and retracting each of said pins individually,
   wherein said device further comprises a computerized mechanism for instructing said controller to shift/retract each of said pins individually, according to a script, being a group of timed instructions represented as commands,
   wherein each command of said script defines a presentation of said pulse/signal, said presentation being selected from a group consisting of: an intensity, a duration, a rhythm, and a cycle,
   thereby generating the physical stimulation pulse/signal to the human body, according to said script;
   thereby allowing treating the depression, anxiety and pain by forwarding to a brain, said physical stimulation pulses/signals resembling said pre-programmed spatial shapes.

2. A device according to claim 1, wherein said pre-programmed shapes being sensible by the touch sense comprise a procedure of increasing resolution of lines formed by said plurality of adjacent dots, thereby utilizing the touch sense for brain discrimination exercises.

3. A device according to claim 2, wherein said procedure of increasing resolution of lines comprises maintaining a constant number of lines.

4. A device according to claim 2, wherein said procedure of increasing resolution of lines comprises providing an equal spacing between lines at each presentation.

5. A device according to claim 2, wherein said procedure of increasing resolution of lines comprises providing a varying spacing between lines at each presentation.

6. A device according to claim 1, wherein said pre-programmed shapes being sensible by the touch sense comprises presentation of empty segments thereof in part, thereby utilizing the touch sense for brain completion exercises.

7. A device according to claim 1, wherein said pre-programmed shapes being sensible by the touch sense comprises a procedure of
providing said line,
then providing a portion of said line, and
then providing a difference in presentation between said line and said portion of said line,
thereby utilizing the touch sense for producing a sensation expectation, produced by said line and by said portion thereof, and for producing a fulfillment of the sensation expectation, produced by said difference in presentation.

8. A device according to claim 1, further comprising a mechanism for heating said plurality of adjacent dots, for allowing said device to produce a heating pulse/signal.

9. A device according to claim 1, further comprising a mechanism for chilling said plurality of adjacent dots, for allowing said device to produce a chilling pulse/signal.

10. A device according to claim 1, further comprising a mechanism for electrifying said plurality of adjacent dots, for allowing said device to produce an electric pulse/signal.

11. A device according to claim 1, further comprising an electromagnetic mechanism, for magnetizing said plurality of adjacent dots, thereby allowing said device to produce a magnetic pulse/signal.

12. A device according to claim 1, wherein each of said dots is heated individually.

13. A device according to claim 1, wherein all of said pins are heated together by a heated liquid disposed around said pins when being in their retreated state.

14. A device according to claim 1, wherein each of said pins is chilled individually.

15. A device according to claim 1, wherein all of said pins are chilled together by a chilling liquid disposed around said pins when being in their retreated state.

16. A device according to claim 1, wherein said pins are adapted to be applied against a surface of the human body.

17. A device according to claim 16, wherein said surface is selected from a group consisting of: a palm, a foot sole, a back, a face.

18. A device according to claim 16, wherein the more sensitive a region of said surface, the higher density of said group of shiftable and retractable pins.

19. A device according to claim 1, wherein said pins are shifted out in a geometric form.

20. A device according to claim 1, wherein said pins are shifted in a partial geometric form, thereby allowing a patient's brain to complete a full geometric form.

21. A device according to claim 1, further comprising:
a first perforated plate wherein said pins are shiftable through the perforation;
a second plate;
a closed space between said plates, filled with a liquid; and
a heating/chilling body disposed in said liquid, for heating/chilling said liquid, thereby heating/cooling all of said pins when dipped in said liquid.

22. A device according to claim 1, wherein said plurality of adjacent dots comprises an electrical mask comprising a plurality of electrical outputting dots.

* * * * *